(12) United States Patent
Soderquist

(10) Patent No.: US 8,388,763 B2
(45) Date of Patent: Mar. 5, 2013

(54) PORTABLE WASHING AND DISINFECTING APPARATUS

(76) Inventor: Karl Soderquist, Goffstown, NH (US)

( * ) Notice: Subject to any disclaimer, the term of this patent is extended or adjusted under 35 U.S.C. 154(b) by 986 days.

(21) Appl. No.: 12/109,393

(22) Filed: Apr. 25, 2008

(65) Prior Publication Data

US 2009/0266381 A1    Oct. 29, 2009

(51) Int. Cl.
*B08B 3/00* (2006.01)
(52) U.S. Cl. .................. 134/57 R; 134/199; 134/200
(58) Field of Classification Search .......... 134/57 R, 134/198, 199, 200
See application file for complete search history.

(56) References Cited

U.S. PATENT DOCUMENTS

| | | | | |
|---|---|---|---|---|
| 2,619,435 A | * | 11/1952 | Flinchbaugh | 134/111 |
| 2,960,990 A | * | 11/1960 | Jones et al. | 134/95.3 |
| 3,542,592 A | * | 11/1970 | Zweig | 134/1 |
| 4,067,691 A | | 1/1978 | McGady et al. | |
| 5,275,668 A | | 1/1994 | Dell et al. | |
| 5,285,802 A | | 2/1994 | Soderquist | |
| 5,669,401 A | * | 9/1997 | Mansur | 134/108 |

FOREIGN PATENT DOCUMENTS

| | | |
|---|---|---|
| GB | 1 344 023 | 1/1974 |
| GB | 2 176 100 A1 | 12/1986 |
| WO | 92/03171 A1 | 3/1992 |

* cited by examiner

*Primary Examiner* — Michael Barr
*Assistant Examiner* — David Cormier
(74) *Attorney, Agent, or Firm* — Robert R. Deleault, Esq; Mesmer & Deleault, PLLC

(57) ABSTRACT

A mobile washing and disinfecting system includes a wash chamber with an openable door, a mobile base coupled to the wash chamber, the mobile base having a recess containing all electromechanical components, a re-configurable spray arm assembly having a pivotable spray arm with a plurality of nozzles connected to a water turbine configured to pivot the spray arm in an oscillating motion for directing a spray of washing and disinfecting fluids radially away from the spray arm within a predefined arc, and a modular programmable microprocessor control supported on the removable wash housing for controlling the cleaning cycles.

20 Claims, 7 Drawing Sheets

PORTABLE WASHING AND DISINFECTING APPARATUS

BACKGROUND OF THE INVENTION

1. Field of the Invention

The present invention relates generally to medical equipment cleaning. Particularly, the present invention relates to a hydro impact equipment cleaning and disinfecting washer.

2. Description of the Prior Art

Medical equipment such as wheelchairs, gurneys, walkers, and the like must often be cleaned and disinfected when used daily in health care facilities. Dirt, food, blood, mucous, and urine are typical substances that collect and build up on many parts of such medical equipment.

The construction of this type of medical equipment poses special problems when cleaning by hand. Various material types such as rubber, plastic, metal and vinyl, plus different sized parts and the number of inter-connecting pieces result in difficult areas to reach when cleaning.

Hand towels, scrub brushes, spray bottles, and shower hoses are typical cleaning utensils that personnel use for hand cleaning. These cleaning utensils require personnel to have direct contact with the equipment when cleaning. With the increasing risk of infectious diseases that can be carried by medical equipment and the general avoidance of having direct contact with unpleasant odor and substances on the wheelchair, personnel tend to avoid thorough cleaning. These factors and conditions often lead to minimum frequency of cleaning and inconsistent quality. General purpose pressure washers and steam cleaners are also used for medical equipment cleaning. Typically, the equipment such as wheelchairs, gurneys and the like are brought to special cleaning areas inside or outside a health care facility to accommodate the wide diffusing of water created by high pressure washing equipment.

While high pressure cleaning is very effective for thorough cleaning, it is disruptive to the medical equipment user since the equipment must be taken from the user during the day when this type of cleaning is typically scheduled and is disruptive to the facility as equipment must be transported by the staff to designated cleaning areas. High pressure cleaning typically uses very hot water and combined with pressure can dissolve grease in the wheel bearings when the spray is directed to the wheel area of the medical equipment. Furthermore, hot water to steam temperatures used by steam cleaners and pressure washers are corrosive to metal tubing that are used in constructing many types of medical equipment. In addition, cleaning quality is dependent on the person using the equipment.

Cleaning outside also causes environmental concern since appropriate drains are not common in parking lots or driveways where cleaning is often done.

There has been devised a portable wheelchair cleaning system that circumvents many of the problems mentioned.

U.S. Pat. No. 5,285,802 (1994, Soderquist) discloses a wheelchair cleaning system. The system includes a modular assembly, a wash chamber, operator control unit, and a mobile base support structure housing the electromechanical components used to apply the cleaning process. The wash chamber includes a rotating spray arm assembly. The rotating spray arm assembly includes a distribution tube connected on one end to a rotary seal housing and is closed off and coupled to a gear housing on the other end. The gear housing is a chain driven gear connected to a gear motor drive. The distribution tube serves as a drive shaft to provided rotary motion to the spray arm assembly. A spray arm is connected to the distribution tube and extends radially away from the rotating axis of the distribution tube. The spray arm has a plurality of spray nozzles for directing a spray of washing and disinfecting fluids.

A disadvantage of the wheelchair cleaning system is the number of drive components required to drive the rotating spray arm assembly. A separate drive motor is required along with the electrical connections necessary for operation. Further, additional water seals to protect the electrical drive motor and its electrical components are required as well as ground-fault protection in the event a seal deteriorates and cleaning water penetrates to the electric motor and/or its electrical components.

Therefore, what is needed is a system that reduces the number of electrical components to operate the washer. What is also needed is a system that is more energy efficient.

SUMMARY OF THE INVENTION

It is an object of the present invention to provide a washing and disinfecting washer system that is more energy efficient than currently available systems. It is another object of the present invention to provide a washing and disinfecting washer system that has fewer electrical motors and corresponding electrical components.

The present invention achieves these and other objectives by providing a mobile washing and disinfecting system for one or more articles which includes a wash chamber having a substantially enclosed interior region for enclosing articles being washed. The wash chamber is supported by a base. A re-configurable spray arm assembly is preferably secured to the wall of the wash chamber but can be positioned any place within the wash chamber, i.e. floor, walls, ceiling. The spray arm assembly includes a water turbine to which is connected a spray arm having a plurality of spray nozzles for directing a spray of wash fluids upon the articles enclosed within the wash chamber and a coupling mechanism used to secure the spray arm assembly to the inside of the wash chamber. The water turbine provides an oscillating action to the spray arm so that the spray arm can rotate through an arc to spray cleaning and rinsing solution over the articles enclosed within the wash chamber to maximize the coverage of the spray of wash fluids over multiple surfaces of the articles. The mobile washing and disinfecting system also includes a re-circulating and filtering system in fluid communication with the wash chamber. The re-circulating and filtering system is preferably housed within the base.

The base includes a base top, which also acts as the wash chamber floor. The base top has a floor opening that aligns with and has attached thereto the top of a sink assembly, which is a part of the re-circulating and filtering system. The sink assembly resides within the base below the base top. The sink assembly includes a floor screen with a floor nozzle port and a sink filter assembly positioned within the sink that divides the sink into a sink front chamber and a sink rear chamber. The removable floor screen collects larger particles. A channel along the edges of the floor screen becomes the collection area as water sweeps along the top and moves particles into the channel. An opening in the center of the floor screen accommodates an underspray nozzle that is within the sink front chamber for under carriage cleaning.

The sink filter assembly includes a filter housing with a filter screen opening and a removable filter screen. The filter housing provides the operator the convenience to easily remove the filter for cleaning. The filter screen, which is preferably a fine mesh filter screen, is positioned in front of the filter housing and collects particles as the wash pump pulls water through the screen into the sink rear chamber and into the wash pump and then out through the spray nozzles of the spray arm assembly.

The filter housing is securely connected to the inside of the sink to prohibit particles from entering into the sink rear chamber and into the pump. The sink rear housing also includes one or more water float switches or sensors. The filter housing includes air vent openings to release vacuum caused by the tight seal between the filter housing and the sink. The filter housing can also be removed from the sink assembly for cleaning.

Float switches protected in the filter housing are used to indicate when there is sufficient water to run cleaning functions and to indicate when the sink is empty during a draining function.

With the initiation of cleaning, water is released into the sink through a spray nozzle that is directed to the back side of the filter screen and removable screen. Particles that have collected on the outside surface of the filter screen are removed by the force of water and later drained out of the sink during the drain function. This self-cleaning function maintains high productivity and saves the cost of continually purchasing filter cartridges.

When the under spray selection is activated, water is diverted by a valve into the water line and out through the under spray nozzle. The nozzle creates a one hundred twenty (120) degree full cone spray pattern for cleaning the inside surface of both back and front wheels of a wheelchair and other equipment that can benefit from a under carriage cleaning function.

In preferred embodiments, the spray arm assembly includes a water turbine and a spray arm connected on one end to the water turbine outlet. The spray arm has a plurality of nozzles and a second end supported by a spray arm support. The water turbine oscillates the spray arm through a pre-defined arc. The spray arm assembly is also removably attached to the inside of the wash chamber wall for easy re-configuration to any position within the wash chamber, i.e. floor, walls, roof/ceiling. The plurality of nozzles direct washing and disinfecting fluids toward the medical equipment to be cleaned and disinfected.

In preferred embodiments, the cleaning apparatus is a portable wheelchair cleaning system where a wheelchair is placed into the wash chamber and is thoroughly cleaned. The wheelchair cleaning system includes a wash chamber with an attached chemical cabinet and electronics compartment mounted on a mobile base containing the electromechanical components for applying the wash, disinfection and rinse functions.

The wash chamber with the attached chemical cabinet and electronics compartment are a modular assembly supported by the mobile base. A primary advantage resulting from the present invention is providing mobility for wheelchair cleaning in different locations of a health care facility. Using standard electrical and water supply outlets found throughout the facility, the cleaning system easily connects to these outlets and provides thorough cleaning with minimal direct contact of the equipment by personnel thereby increasing the likelihood of frequent wheelchair cleaning.

Cleaning functions are selected using an operator's panel located on top of the wash chamber. Cleaning functions include a quick wash, normal wash, long wash and a rinse function. In addition to the cleaning functions, disinfectant solution can be included, a no-foam solution to control suds, an underspray function, parts cleaning and final rinse with rinse additives that speed up the drying process.

Containers located in the chemical cabinet are used to hold concentrated cleaning detergents, disinfectant, anti-foaming agent(s), rinse additives and cleaning detergents for an optional spray attachment. A tubing line connects to a coupling with a stem into the container and feeds into a valve that opens under program control. A metering pump draws a measured amount of liquid chemical into the sink for the washing, disinfecting, anti-foaming or rinsing cycles.

An advantage of the present invention is that the microprocessor controls dilution rate of chemicals used for cleaning, disinfecting and rinsing. Personnel are free from directly handling concentrated chemicals. Of particular importance is the application of disinfecting solution. Current methods of using hand held spray containers to apply disinfectants to equipment often require the user to mix their own solution of disinfectants and water, and as result, may have dilutions that do not meet standards for disinfecting.

Measuring and controlling the dilution mixture for chemicals also provides for the optimum efficiency in cleaning results and controlling costs.

With the initiation of the cleaning selection, the water supply line is opened by a valve and hot water is released into a sink located in the base structure. Float level switch(es)/sensor(s) monitored by the programmable software determines the amount of water that will be used in the wash and rinse cycles. A measured amount of detergent is released into the sink through a valve in a line that is connected to the detergent solution container.

A wash pump draws the mixed solution in the sink through a line into the rotating spray arms and out through spray nozzles located on the spray arms. By positioning the oscillating spray arms in different locations in the wash chamber, the wheelchair can be surrounded on all four sides to provide maximum coverage on areas of a wheelchair that often collect contaminants. As the spray arms oscillate across the wheelchair, the spray under pressure makes contact with all surfaces.

In the preferred embodiment of the oscillating spray arms, couplings are located on the spray arm assembly that allow the spray arm assembly position to be easily changed as desired. Couplings located on the spray arm assembly can be disconnected so that the rotating spray assemblies can be placed in different locations in the wash chamber for different shape and size of equipment. This ability to easily re-configure the position of the spray arm assembly makes the present invention suitable as a cleaning apparatus for devices and articles other than medical equipment. For example, cleaning articles such as screens or helmets can also benefit from the present invention. Because the spray arms are re-configurable within the wash chamber, almost any conceivable article or plurality of articles or equipment can be easily cleaned and/or disinfected. In addition to changing the oscillating spray assembly position, the number of spray nozzles on the spray arm can be increased or decreased to affect spray pressure and coverage. Water pressure through the nozzles will assist in dislodging contaminates collected on various parts of the equipment or articles.

The preferred embodiment uses hot water commonly found in utility sinks or room sinks with a regulated water temperature of 110° F. to 120° F. degrees. Spray pressure produced by the wash pump is less than 100 psi. These factors reduce the dissolving of grease on wheel bearings that typically occur with high pressure and very hot water in excess of 140° F. Wheelchairs are constantly in need of cleaning and the use of high pressure and very hot water on a continuous basis results in replacing wheel bearings due to grease being dissolved and the corrosive factors inherent with the use of very hot water.

A filter housing located in the sink is placed into the wash pump line to trap contaminants from entering the wash pump and subsequently clogging spray nozzles as well as protecting the wash pump impellers. To remove contaminants lodged on the filter screen without direct user contact, the water supply line extends into the filter area. When filling the sink with water for the wash and rinse cycles, water is sprayed against the inside of the filter screen forcing the collected contaminants on the outside of the filter screen into the sink to be sucked into the drain opening during the drain process.

The advantage of the present invention is the continuous cleaning of the filter thereby minimizing any direct contact by the user in handling contaminants as a result of the cleaning process. Another advantage of the continuous cleaning is maintaining high production cleaning by not having to stop and replace or clean the filter in addition to saving costs by not having to purchase replaceable filters.

Another benefit of the wash chamber is that no electromechanical parts used in the cleaning process are designed into the wash chamber. The wash chamber is simply an enclosure that mounts onto the base and therefore can be made out of various material for lightness, molding and transportability without regard to any connecting or mounting components used in the application of cleaning.

Construction of a wash chamber that is not dependent on any electromechanical components used for applying the cleaning process also provides for alternative sized wash chambers to accommodate other equipment.

Preferably, the micro-processor may be programmed to provide enhancements and updates to the system. For example, if new chemicals are introduced that require a change in dilution ratios, software changes can be made for valve opening time. Measuring and determining the amount of water for different types of equipment cleaning may be changed to accommodate equipment sizes. Pressure and water flow rates may be measured to determine pump efficiency. Water temperature may be monitored.

Use of a water motor turbine has many advantages over the prior art. By modifying and adapting the rotating assembly on a water motor turbine, a spray pipe is configured with a limited number of spray nozzles to reach longer distances of spray coverage while maintaining adequate spray pressure for effective cleaning while conserving water. Spray nozzles are available in many variations designed for specific purposes. For cleaning, the spray pattern for the most impact over a surface is called a flat fan. It is a narrow spray pattern with various lengths. The spray arm is adjustable to oscillate from 180° to 10°. Spray arms of the present invention can also be configured with anywhere from one nozzle to multiple nozzles. For example, if one area requires additional flow and pressure, the spray system could use one nozzle that has a wider opening for more flow of water and pressure resulting in better cleaning.

Prior art systems that use a fixed nozzle approach are faced with either using many flat fan nozzles to get the coverage required or using a cone type nozzle that has less spray pressure impact. As the number of nozzles increase then the spray pressure goes down or one has to use a bigger pump requiring more electricity. The rotating systems used in the prior art use electro-mechanical devices, motors and bearings that have to be in a particular position. In addition, these mechanical devices are typically housed in a dry area away from the water furthering the restrictions to being easily re-configurable as compared to a water motor that resides in the wet environment.

Since the mechanism to drive the oscillation of the spray nozzles of the present invention is only dependent on water flow to the gear driven water turbine, spray pipes can be placed in any location within the area that durable medical equipment is placed for cleaning, disinfecting and rinsing.

As long as there is a water source distribution line under pressure, a rotating assembly can be used for effective cleaning without the requirement of expensive electrical motor driven mechanisms.

In addition to any location, the spray pipes can be placed in any orientation; horizontal, vertical or angled to line up with equipment shape or size for effective cleaning, disinfecting or rinsing. The rotation of the spray pipe provides for the use of flat fan spray nozzles producing better cleaning higher impact per square inch. Advantageously, the wash chamber may be sized to accommodate various types of medical equipment such as, for example, wheelchairs, carts, stretchers, gurneys, hospital beds, and the like.

This approach offers the opportunity to provide a very effective cleaning apparatus at a very low cost. The use of motor driven mechanisms to rotate spray nozzles positioned on water feed pipes is a major disadvantage since they are outside of the wash chamber and are not easily re-configurable. In addition, motor drive mechanisms are expensive and require electrical wiring, switches, motor, bearings and logic controllers for determining direction of rotation.

DETAILED DESCRIPTION OF THE PREFERRED EMBODIMENT

Figure 1:
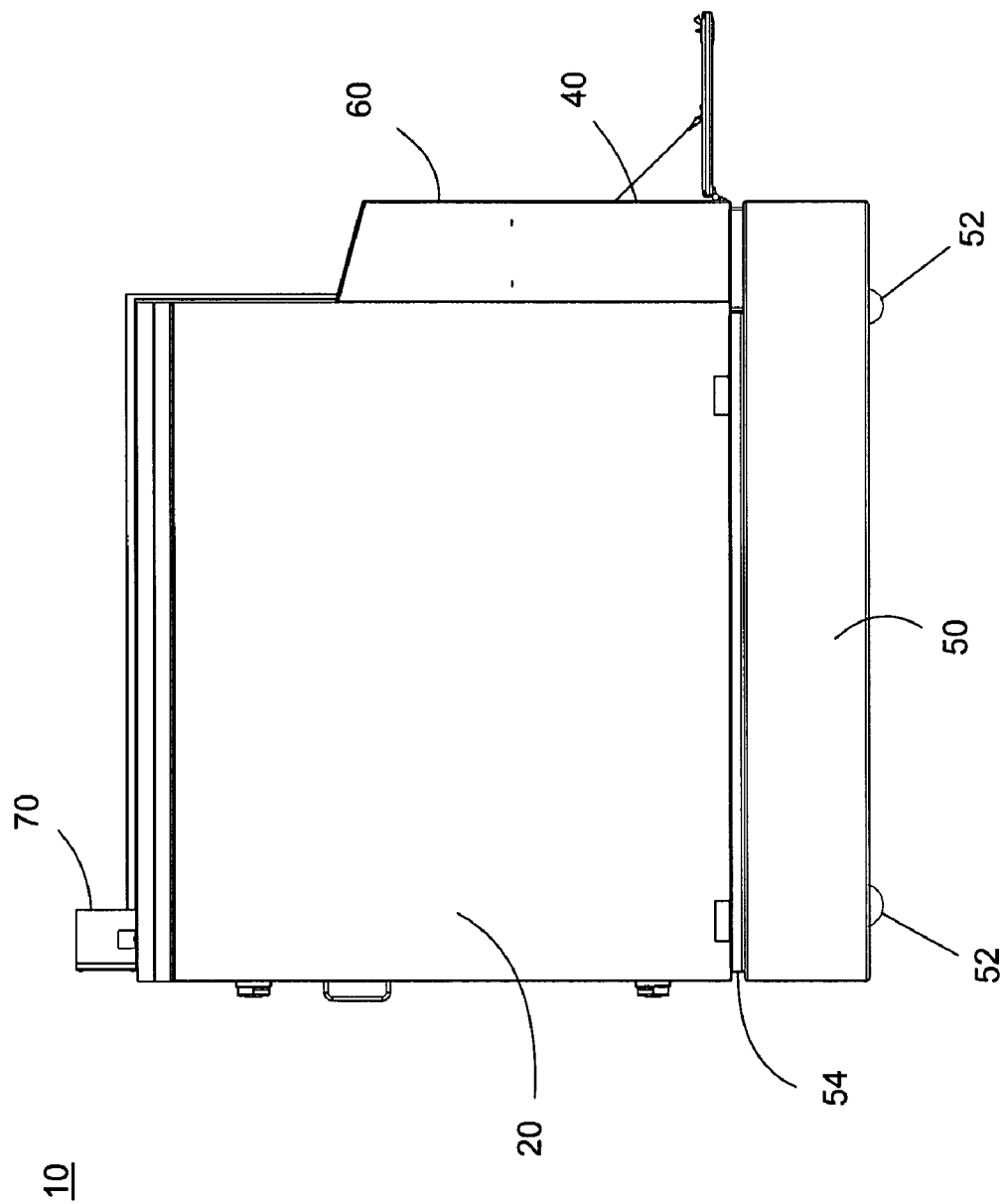
FIG. 1 is a side view of the present invention showing one embodiment of the mobile washing and disinfecting system.

The preferred embodiment(s) of the present invention is illustrated in FIGS. 1-8. A mobile washing and disinfecting system 10 for medical equipment used for supporting the weight of a patient embodying the present invention is shown in FIG. 1. The mobile washing and disinfecting system 10 includes a wash chamber 20, a chemical cabinet 40, an electronics compartment 60, and a control panel 70 supported and mounted on a mobile base 50. Caster wheels 52 provide for mobility. Mobile washing and disinfecting system 10 is preferably made of aluminum. This material provides for minimum weight for mobility and removing the wash chamber off the base. Alternatively, construction can be fabricated using stainless steel, plastics and other material based upon operating environment and costs.

Figure 2:
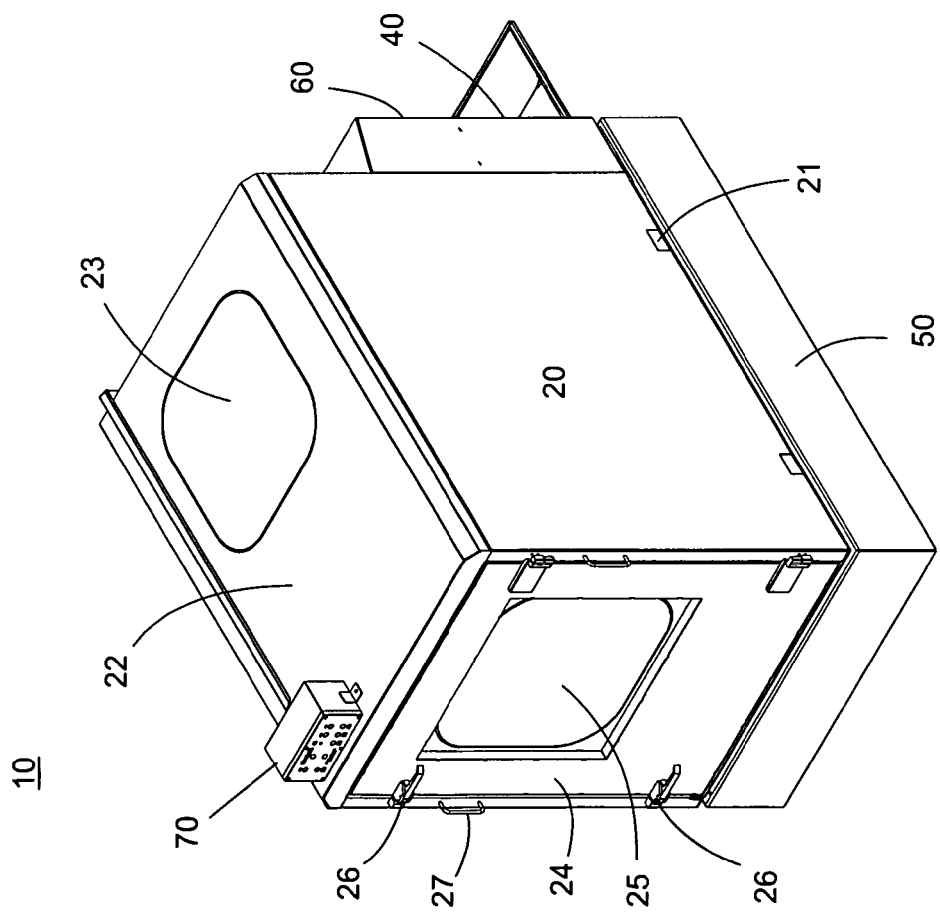
FIG. 2 is a perspective view of the embodiment shown in FIG. 1.

A more detailed view of wash chamber 20 is shown in FIG. 2. Wash chamber 20 includes a top 22 with a roof window 23 and four sides. One of the sides has a wash chamber door 24. Wash chamber door 24 has a door window 25 for observing the entire wash process if desired. Wash chamber door 24 includes compression latches 26 providing a water tight enclosure when closed against the door seal. Mobility handles 27 are used to move mobile washing and disinfecting system 10. The bottom of wash chamber 20 is open and, when coupled to the mobile base 50, forms the floor for the equipment to be placed on for cleaning. Dimensions for the wash chamber may be any size desired but, if designed for wheelchairs, the dimensions are approximately 49 inches high, 38.5 inches wide and 54 inches deep.

Figure 3:
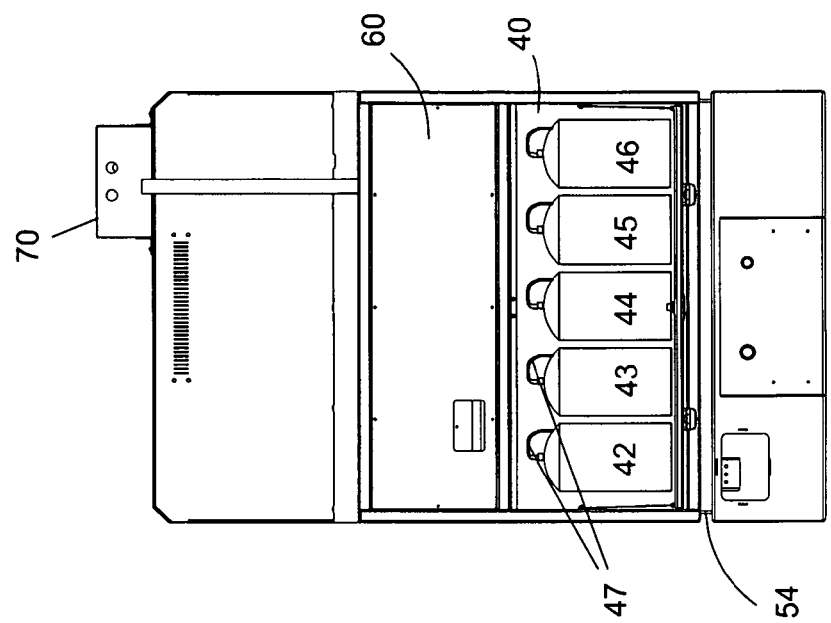
FIG. 3 is a rear view of the embodiment shown in FIG. 1.

Turning now to FIG. 3, there is shown a back view of wash chamber 20. Attached to the back of wash chamber 20 are electronics compartment 60 containing a micro processor, chemical cabinet 40, and a plurality of containers for cleaning detergent 42, disinfectant 43, anti-foaming agent 44, a drying aid 45 and the chemical 46 for the spray attachment. Each of the five containers has a tubing line 47 attaching to a cap coupling with a stem extending into the container to draw the liquid. Each tubing line connects to a valve that will be energized under program control to open and release the concentrated chemical liquid into a sink assembly 80 shown in FIG. 4.

The wash chamber 20 is mounted on the mobile base 50, a recessed ledge around the bottom of the walls of wash chamber 20 are configured to mate with a raised angle edge 54, which provides the means for the wash chamber to fit on the base 50 inside the raised edge. Alternatively, if other sized wash chambers were to be constructed, it should be understood that the same coupling dimensions would be adhered to. Larger sized wash chambers would be constructed with a floor for those areas that exceed the coupling dimensions. In the alternative, base 50 could also be made larger as well.

Figure 8:
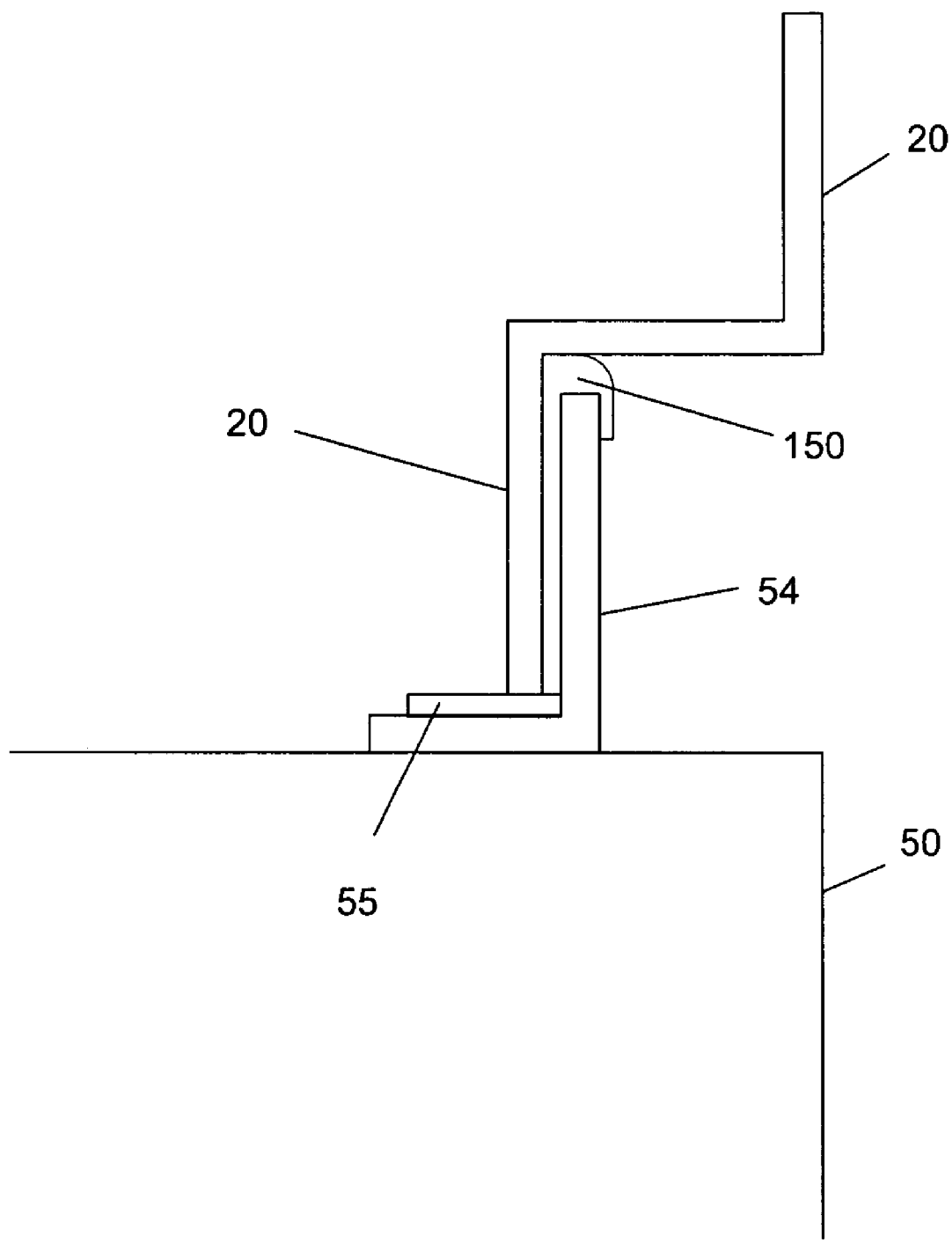
FIG. 8 is an illustrative view of the mobile base coupling design with the removable wash chamber.

Pressure brackets 21 located near the bottom edge of the wash chamber 10 are secured to the base 50 to prevent water leakage by pressing the edges of the wash chamber 20 into a seal 55 shown in FIG. 8 located on the base 50. Additionally, the pressure brackets provide stability for the wash chamber 20.

Shown in FIGS. 1 and 3 to further increase the understanding of coupling the wash chamber 10 to the base 50 is a raised edge 54, approximately one inch in height.

The control panel 70 includes a plurality of switches for selecting cleaning functions and for adding disinfectants and rinse additives. Start, stop and problem switches are included in control panel 70. Alternatively, control panel 70 may add different switches for enhancements to the equipment cleaning process or different size equipment.

Figure 4:
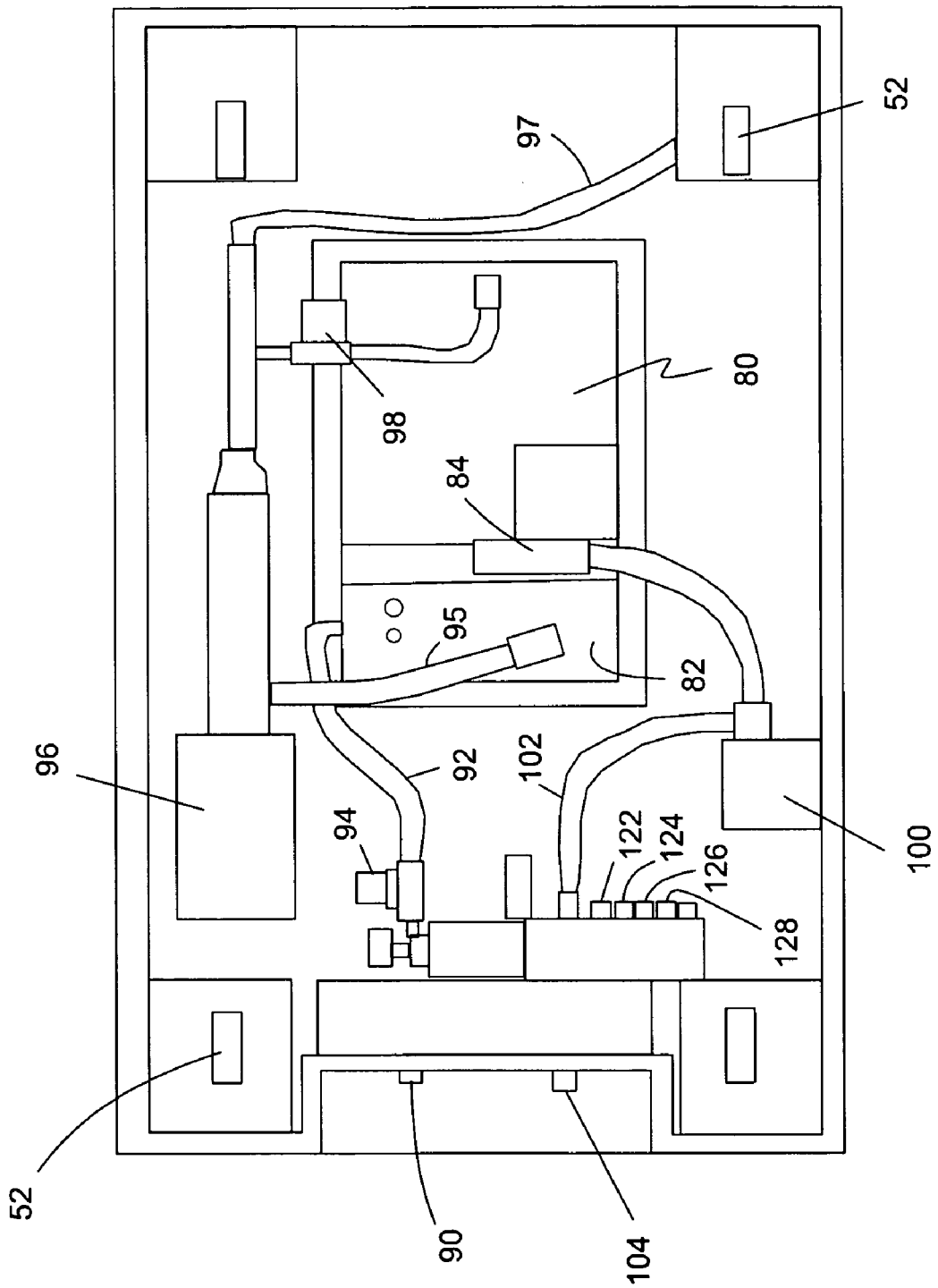
FIG. 4 is a bottom view of the embodiment in FIG. 1 showing the electro-mechanical components in the base.

The base 50 shown in FIG. 4 contains all of the electromechanical components used in the cleaning process. Caster wheels 52 are located on the front and back for mobility.

Water from the water supply connection 90 enters the sink assembly 80 through the water supply line 92. The solenoid valve 94 under program control will open and release a measured amount of water into the sink assembly 80. Approximately three (3) gallons of water are used for the wash and rinse cycles. During the last rinse cycle, water remains in the sink to be used for the next wash cycle. If disinfectant solution was applied to the medical equipment such as a wheelchair, water remaining in the sink would be drained out due to the disinfectant solution mixing with the cleaning detergent and creating a high foaming reaction. Once the measured amount of water has been reached, determined by a flow level switch, solenoid valve 94 will close.

With water now in sink assembly 80, a measured amount of detergent stored in the detergent container 42 shown in FIG. 3 will be released into the sink assembly 80 by opening the detergent solenoid valve 122 under program control. The detergent is released into the sink assembly 80 by gravity feed as the detergent container is located higher than the sink. Standard detergents used by general purpose pressure washing equipment or hand cleaning should not be used with the cleaning system due to the high foaming characteristics of those detergents. High foaming is due to water pressure, small spray nozzle openings and water passages thereby increasing aeration of the water which substantially decreases pump performance. Very low foaming detergents must be used.

During the rinse cycles, of which there are two, a measured release of disinfectant solution through the disinfectant solenoid valve 124 and/or anti-foaming agent solution through anti-foaming agent solenoid valve 126 and/or drying agent solution 48 through drying agent solenoid valve 128 will occur if selected by the operator at control panel 70 shown in FIG. 3.

The wash pump 96 draws water from the bottom of the sink 82 through a line 95 connected to sink 82 and out through pump line 97 into a fluid distribution line 130 within wash chamber 20 that is connected to a spray arm assembly 140 for distribution of water into the spray arm and out through spray nozzles to return into the sink assembly 80 for re-circulating the water used in the wash or rinse cycles. A centrifugal booster pump is used as the wash pump 96 to provide pressure washing.

Once the wash or rinse cycles are completed, the drain pump 100 draws water from the bottom of the sink assembly 80 using a different opening out through the drain line 102 and drain connection 104 into a floor or utility sink drain that is adjacent to the unit. A dishwasher pump and motor is used as the drain pump 100 for high flow rate and to accept contaminants such as food remains that have collected on the wheelchair.

Figure 5:
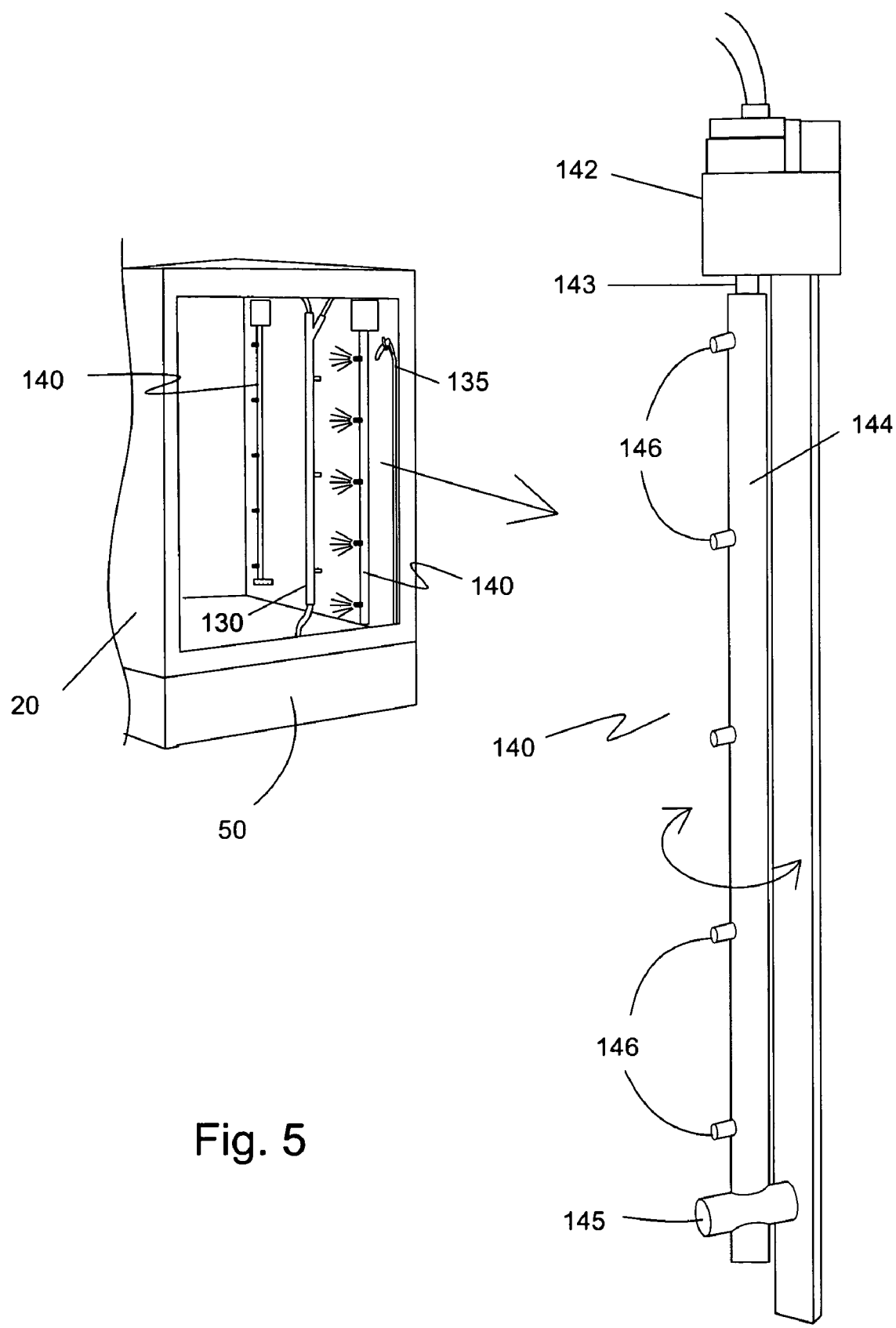
FIG. 5 is a perspective view of the embodiment in FIG. 1 showing a vertical embodiment of the spray arm assembly within the wash chamber and an enlarged view of the spray arm assembly.

In FIG. 5, water from the wash pump 96 enters the fluid distribution line 130, which is preferably secured in place with one or more distribution line supports, and splits its flow into the left and right spray arm assemblies 140. The flow of water will then enter into a water turbine 142 and out to the spray arms 144.

Each spray arm 144 has a plurality of spray nozzles 146 strategically positioned on spray arm 144 to maximize cleaning results. The openings in the plurality of nozzles 146 serve as a system release for the water circuit to allow system flow and recirculation. Spray nozzles are available in many variations designed for specific purposes. For cleaning, the spray pattern for the most impact over a surface is called a flat fan. It is a narrow spray pattern with various lengths. The spray arm 144 is adjustable to oscillate from 180° to 10°.

Water turbine 142 uses the flow of water to cause a turbine output tube 143 to oscillate through a predefined arc. In the preferred embodiment, a commercially available water turbine is adapted for use in the present invention. A usable water turbine is model number 9836Z and available from Gilmour Manufacturing, Somerset, Pa. One end of spray arm 144 is connected to turbine output tube 143 and the other end is rotatably supported by a spray arm support 145. Turbine output tube 143 causes spray arm 144 to pivot in an oscillating motion through the predefined arc for directing a spray of washing and disinfecting fluids radially away from spray arm 144 out the plurality of nozzles 146. Typically, wash chamber 10 will have at least two, one on opposite sides of wash chamber 10, but preferably four, two being space from each other on opposite sides of wash chamber 10.

Although spray arm assembly 140 is shown in a vertical position, it should be understood that spray arm assembly 140 may be oriented in a horizontal position or any position in between. Thus, it is preferable to make spray arm assembly 140 removable to facilitate the installation of other medical type equipment or odd sized appliances to be cleaned which may present either interference to the spray arm oscillation or less effective cleaning and disinfection. Also illustrated is an optional spray attachment 135 for manually spraying selected areas of the medical equipment.

Additionally and optionally, each spray arm assembly 140 may have a solenoid valve for opening and closing the water line connected to water turbine 142. This provides the further advantage of controlling the water flow to the spray arm assemblies 140 in order to maintain high water pressure and flow for each assembly. This is particularly useful for cleaning large items such as stretchers.

In another embodiment, such as a larger wash chamber, it may be desirable to oscillate through either more or less angle. It should be understood that this angle can be changed by adjustments in the water turbine.

Figure 6:
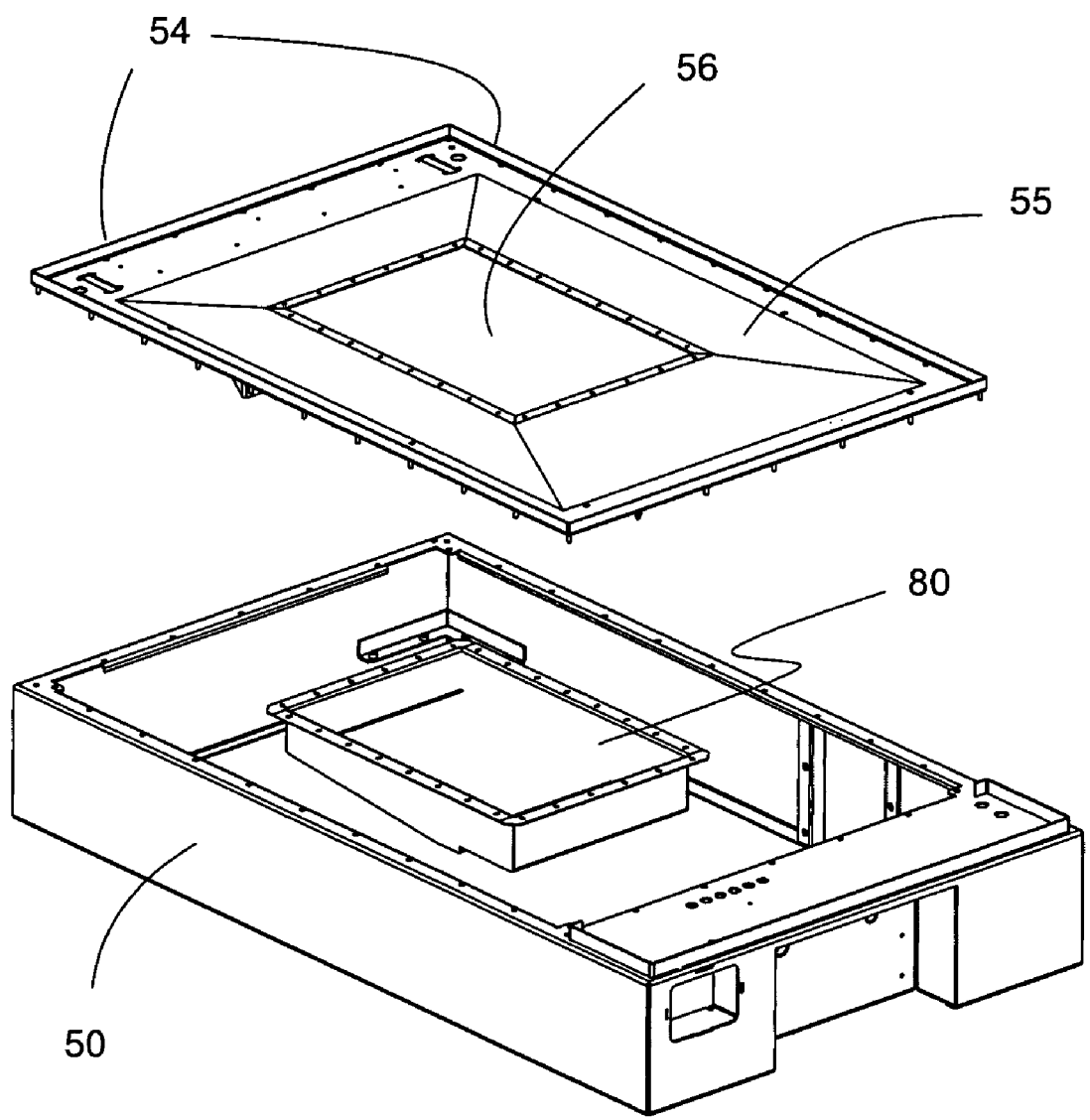
FIG. 6 is an exploded, perspective view of the base of the present invention showing the sink assembly.
Figure 7:
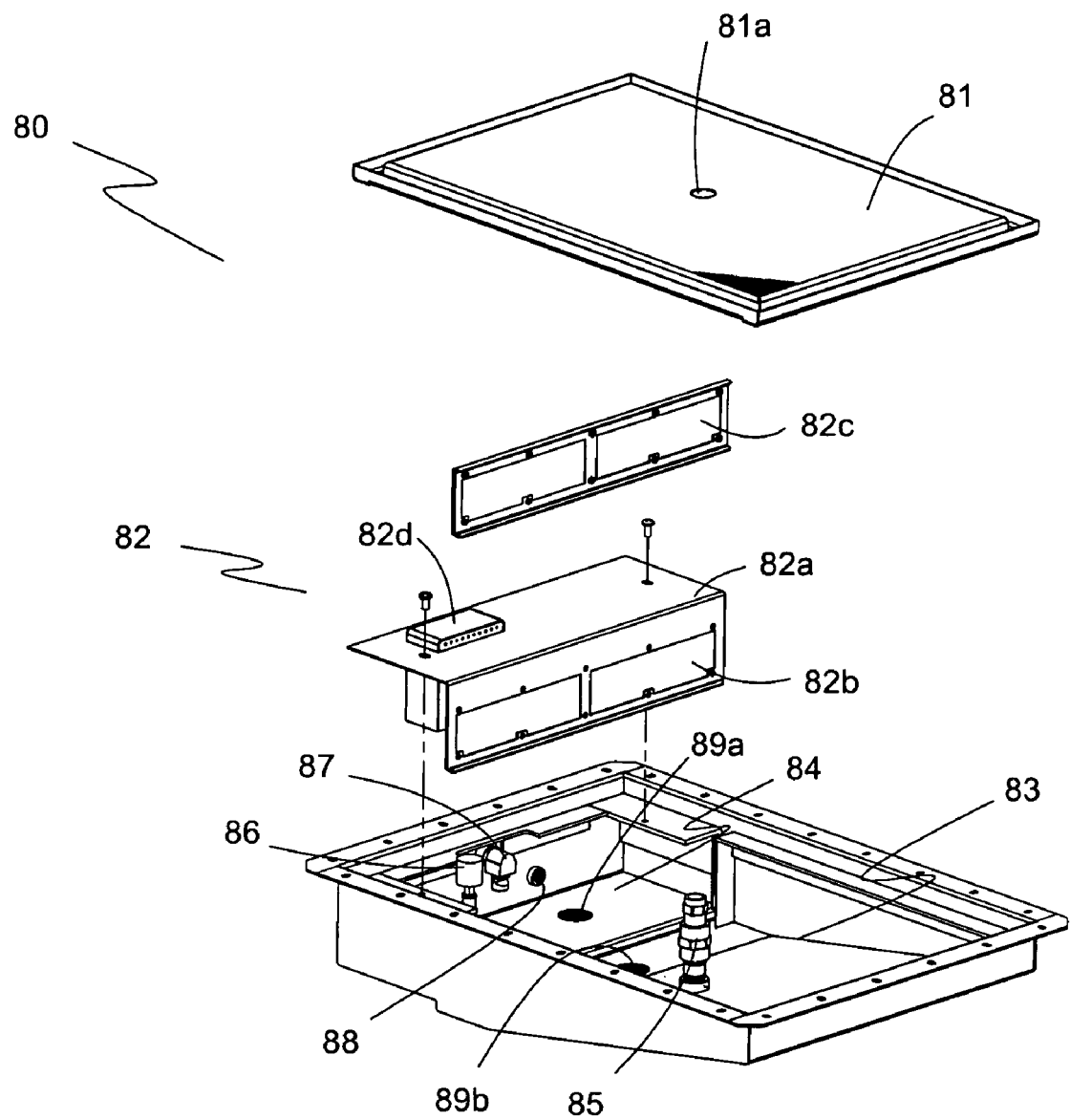
FIG. 7 is an exploded, perspective view of the sink assembly used in the embodiment of the present invention shown in FIG. 1.

FIG. 6 is a perspective, exploded view of base 50 and sink assembly 80 located within base 50. Base 50 has a base top 55, which forms the floor of wash chamber 10. Base top 55 has a floor opening 56 that accommodates the top of sink assembly 80. FIG. 7 is a perspective, exploded view of sink assembly 80. Sink assembly 80 includes a floor screen 81 with a floor nozzle port 81a, a sink filter assembly 82 positioned within sink assembly 80 dividing sink assembly 80 into a sink front chamber 83 and a sink rear chamber 84, and a floor spray nozzle 85 positioned within sink front chamber 83 below and aligned with floor nozzle port 81a. Sink filter assembly 82 includes a filter housing 82a, a filter screen opening 82b, a filter screen 82c positioned in filter screen opening 82b, and a filter assembly vent 82d. Sink filter screen 82c is disposed between sink front chamber 83 and sink rear chamber 84. Sink filter screen 82c and floor screen 81 are preferably removable for easy replacement in the event of damage to the screens.

Sink rear chamber 84 contains a high and low water sensor 86 and a wide angle spray nozzle 87 for cleaning the filter screen 82c. High and low water sensor 86 signals the valve 94 to close as the measured amount of water has been reached for wash and rinse cycles. Sink rear chamber 84 also includes a chemical dispensing outlet 88 and a wash pump outlet 89a in fluid communication with wash pump 96. Sink front chamber 83 has a drain pump outlet 89b in fluid communication with drain pump 100. When wash pump 96 draws water from wash pump outlet 89a, water flows through filter screen 82c. This prevents contaminants and large objects from entering into wash pump 96, which is a centrifugal pump in the preferred embodiment and which is not designed for solids, and reduces any clogging of spray nozzles 146 located on the spray arm assembly 140. Optionally, additional strainers can be incorporated into the water lines before water turbine 142 to further prevent damage to the water turbine gears in the event the sink filter screen 82c is inadvertently left out.

During the re-circulation of water, contaminants will collect on filter screen 82c due to the suction force of wash pump 96. Filter screen 82c covers a large area within the sink to prevent total clogging of filter screen 82c for each wash or rinse cycle.

When the cycle is completed, drain pump 100 will drain out the water through drain pump outlet 89b and contaminants that are floating in the sink water. Near the end of the drain process determined by water sensor 86 for low water, the water supply line 92 will be opened by energizing the valve 94 to open and spray nozzle 87 that is attached to the water supply line positioned inside the sink rear chamber 84 will spray against the contaminants on filter screen 82c and force them off into sink front chamber 83 to be sucked down into drain pump outlet 89b. This contaminant cleaning of filter screen 82c occurs for each wash and rinse cycle thereby maintaining minimum operator cleaning of filter screen 82c.

Sink assembly 80 is designed to slope downwards into wash pump outlet 89a and drain pump outlet 89b to increase flow of water for recycling in the wash and rinse cycles.

In FIG. 8, the coupling of wash chamber 10 and base 50 is illustrated in detail. The edge of wash chamber 10 comes down and across the raised edge 54 and down again onto a seal 55 mounted on base 50. This coupling design is used for all four sides. On top of the raised edge 54, an additional seal 150 is used to prevent water leakage.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A mobile washing and disinfecting system for cleaning one or more articles, the system comprising:
    a wash chamber with an openable door;
    a mobile base coupled to the wash chamber, the mobile base having a recess containing a plurality of electromechanical components;
    a re-configurable spray assembly disposed within the wash chamber, the re-configurable spray assembly having a water turbine directly connected to a wall of the wash chamber and a pivotable spray arm with a plurality of nozzles, the spray arm being substantially linear from a first end to a second end and having the first end directly connected to and extending from the water turbine, the second end connected to the wall, the water turbine configured to pivot the spray arm in an oscillating motion around a longitudinal axis vertically extending from the first end to the second end, of the spray arm for directing a spray of washing and disinfecting fluids radially away from the spray arm within a predefined arc; and
    a modular programmable microprocessor control supported on the wash chamber for controlling the cleaning cycles.

2. The system of claim 1 wherein the openable door has a window.

3. The system of claim 1 wherein the wash chamber has a window.

4. The system of claim 1 further comprising a manual spray attachment supported within the wash chamber.

5. The system of claim 1 further comprising a re-circulating and filtering system in fluid communication with the wash chamber.

6. The system of claim 5 wherein the re-circulating and filtering system includes a floor screen, a wash pump and a drain pump.

7. The system of claim 6 wherein the re-circulating and filtering system further includes a sink assembly below the floor screen wherein the sink assembly contains a chemical dispensing outlet, a wash pump outlet, a drain pump outlet, and an under spray nozzle.

8. The system of claim 7 wherein the sink assembly further includes a sink front chamber and a sink rear chamber having a filter screen disposed between the sink front chamber and the sink rear chamber.

9. The system of claim 8 wherein the sink rear chamber has a wide angle spray nozzle positioned to spray the filter screen.

10. The system of claim 1 further comprising a chemical cabinet connected to the wash chamber.

11. The system of claim 1 further comprising an electronics compartment connected to the wash chamber.

12. A method of washing and disinfecting one or more articles using the mobile washing and disinfecting system of claim 1, the method comprising:
placing the one or more articles within the wash chamber of the mobile washing and disinfecting apparatus; and
delivering a cleaning and disinfecting solution to the re-configurable spray assembly disposed within the wash chamber.

13. The method of claim 12 further comprising connecting a water supply to the mobile washing and disinfecting apparatus.

14. The method of claim 12 further comprising activating the modular programmable microprocessor control supported on a removable wash housing for controlling the cleaning cycles.

15. The method of claim 12 further comprising cleaning a sink assembly filter of the mobile washing and disinfecting apparatus during a wash cycle.

16. The method of claim 12 further comprising cleaning a sink assembly filter of the mobile washing and disinfecting apparatus during a rinse cycle.

17. The method of claim 12 further comprising re-configuring the position of the spray arm assembly disposed within the wash chamber to optimize the cleaning process for the shape of the articles to be cleaned.

18. A mobile washing and disinfecting system for medical equipment used for supporting the weight of a patient, the system comprising:
a wash chamber with an openable door;
a mobile base coupled to the wash chamber having a volume to accommodate medical equipment used for supporting the weight of a patient, the mobile base having a recess containing a plurality of electromechanical components;
a re-configurable spray assembly disposed within the wash chamber having a water turbine directly connected to a wall of the wash chamber and a pivotable spray arm with a plurality of nozzles, the spray arm being substantially linear from a first end to a second end and having the first end directly connected to and extending from the water turbine, the second end connected to the wall, the water turbine configured to pivot the spray arm in an oscillating motion around a longitudinal axis vertically extending from the first end to the second end of the spray arm for directing a spray of washing and disinfecting fluids radially away from the spray arm within a predefined arc; and
a modular programmable microprocessor control supported on the wash chamber for controlling the cleaning cycles.

19. The system of claim 18 further comprising a re-circulating and filtering system having a sink assembly below a floor screen wherein the sink assembly has a sink front chamber and a sink rear chamber having a filter screen disposed between the sink front chamber and the sink rear chamber, the sink rear chamber containing a chemical dispensing outlet, a wash pump outlet, and a wide angle spray nozzle wherein the wide angle spray nozzle is positioned to spray the filter screen, the sink front chamber containing a drain pump outlet.

20. The system of claim 19 wherein the sink front chamber further contains a spray nozzle directed to spray upwardly through a floor nozzle port in the floor screen.

* * * * *